United States Patent [19]

Petersen

[11] 4,262,121
[45] Apr. 14, 1981

[54] HEXAHYDROPYRIMID-4-YL ETHERS AND THEIR PREPARATION

[75] Inventor: Harro Petersen, Frankenthal, Fed. Rep. of Germany

[73] Assignee: BASF Aktiengesellschaft, Fed. Rep. of Germany

[21] Appl. No.: 88,068

[22] Filed: Oct. 24, 1979

Related U.S. Application Data

[62] Division of Ser. No. 40,223, May 18, 1979, abandoned.

[30] Foreign Application Priority Data

Jul. 14, 1978 [DE] Fed. Rep. of Germany ....... 2830997

[51] Int. Cl.³ .................. C07D 401/12; C07D 401/14
[52] U.S. Cl. .................................. 544/296; 544/309; 544/311; 544/314
[58] Field of Search ................ 544/296, 309, 311, 314

[56] References Cited

U.S. PATENT DOCUMENTS

| | | | |
|---|---|---|---|
| 3,502,672 | 3/1970 | Petersen et al. | 544/309 |
| 3,597,147 | 8/1971 | Bille et al. | 544/314 |
| 3,953,505 | 4/1976 | Schibler et al. | 544/314 |

*Primary Examiner*—Paul M. Coughlan, Jr.
*Attorney, Agent, or Firm*—Keil & Witherspoon

[57] ABSTRACT

Novel hexahydropyrimid-4-yl ethers and a process for the preparation of hexahydropyrimid-4-yl ethers by reacting hexahydropyrimidines with alcohols at above 110° C.

The hexahydropyrimid-4-yl ethers obtainable by the process of the invention are valuable starting materials for the preparation of dyes, pesticides and assistants for use in textile chemistry, surface-coating resin chemistry and the timber industry.

1 Claim, No Drawings

HEXAHYDROPYRIMID-4-YL ETHERS AND THEIR PREPARATION

This is a division, of application Ser. No. 40,223, filed May 18, 1979, now abandoned, the entire specification of which is incorporated by reference.

The present invention relates to novel hexahydropyrimid-4-yl ethers and to a process for the preparation of hexahydropyrimid-4-yl ethers by reaction of hexahydropyrimidines with alcohols at above 110° C.

A process for the preparation of 2-oxo(thiono)-hexahydropyrimid-4-yl ethers by reacting ureas with aldehydes in the presence of an acid at below 110° C. has been disclosed (Synthesis 1973, pages 262–263; German Pat. No. 1,231,247). It is stated that the reaction must be carried out with a large excess of alcohol in order to achieve yields which are satisfactory for industrial applications. If acid-sensitive alcohols, eg. oxyethylated carboxylic acids, unsaturated carboxylic acids containing hydroxyl groups, polyalcohols or polyether-diols are employed, the above method of preparation does not give any substantial amount of end product. The neutralization of the acid and the removal of the salts thereby produced are further aspects which make working up difficult.

German Laid-Open Application DOS No. 1,770,089 discloses a process for the preparation of fluorinated 4-alkoxypropyleneureas by reaction of 4-alkoxy(hydroxy)-propyleneureas with fluorinated aliphatic alcohols in the presence of a non-oxidizing acid. It states that the reaction is as a rule carried out at from 20° to 100° C., preferably at from 40° to 80° C.

We have now found that a hexahydropyrimid-4-yl ether of the formula

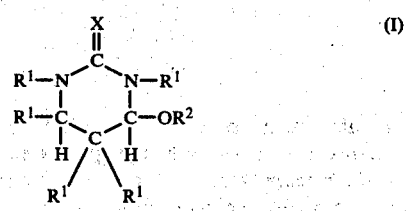
(I)

where the individual radicals $R^1$ and $R^2$ may be identical or different and each is a cycloaliphatic or araliphatic radical, and the radicals $R^1$ may also each be hydrogen or an aromatic or aliphatic radical, and $R^2$ may also be an aliphatic radical which may in addition contain n radicals

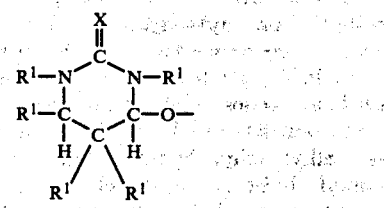

n is an integer from 1 to 5, and X is oxygen or sulfur is obtained in an advantageous manner by reaction of a 4-hydroxy-hexahydropyrimidine or one of its ethers with an alcohol, if a hexahydropyrimidine of the formula

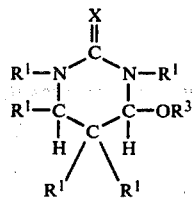
II where $R^1$ and X have the above meaning and $R^3$ is hydrogen and, if $R^2$ is an aliphatic radical of at least 5 carbon atoms or a cycloaliphatic or araliphatic radical, may also be alkyl of 1 to 3 carbon atoms, is reacted, at above 110° C., with an alcohol of the formula $R^4$—OH     III where $R^4$ has the above meanings of $R^2$, or, if $R^2$ is an aliphatic radical containing n radicals

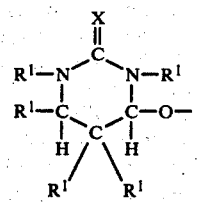

$R^4$ may be the same aliphatic radical with n radicals —OH instead of the n radicals

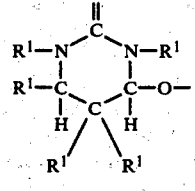

Further, we have found the novel polyhexahydropyrimid-4-yl ethers of the formula

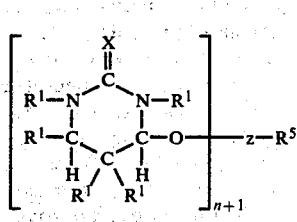
Ia where the individual radicals $R^1$ may be identical or different and each is hydrogen or an aliphatic, cycloaliphatic, araliphatic or aromatic radical, X is oxygen or sulfur, n is an integer from 1 to 5, z is a number of single bonds corresponding to n+1 and $R^5$ is an aliphatic radical.

Where methylglycol and 2-oxo-4-hydroxy-5,5-dimethyl-6-isopropylhexahydropyrimidine are used, the reaction may be represented by the following equation:

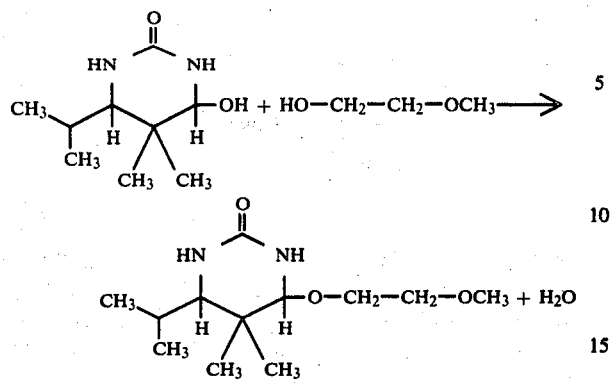

Compared to the prior art, the process of the invention gives a large number of known and of previously not described hexahydropyrimid-4-yl ethers in a simple and economical manner, and, in the case of the known compounds, in better yield and higher purity. It is not necessary to carry out the reaction in the presence of an acid and hence neutralization and the removal of salts are not involved. Decomposition reactions and side reaction of the starting materials and end products are avoided. An excess of the alcohol component is not needed; hence, a substantially improved space-time yield is achieved. All these advantageous results are surprising in view of the prior art. In particular, the higher reaction temperature would have led to the expectation of far greater decomposition of the reaction mixture, and of the formation of heterogeneous mixtures of decomposition products and by-products.

The starting materials II and III can be reacted in the stoichiometric amount or using an excess of either component over the other; preferably, a ratio of from 0.6 to 1, especially from 0.9 to 1, mole of starting material II is used per hydroxyl group and per mole of starting material III. The alcohol used may be a mono-, di-, tri-, tetra-, penta- or hexa-alcohol. Depending on the molar ratio of the starting material II to the starting material III, the products are, accordingly, mono-, di-, tri-, tetra-, penta- and hexa-hexahydropyrimid-4-yl ethers or, if less starting material II than corresponds to the above ratios is used, products ranging from monohydroxypoly-hexahydropyrimid-4-yl ethers to polyhydroxy-mono-hexahydropyrimid-4-yl ethers. Preferred starting materials II and III and, accordingly, preferred end products I are those in which the individual radicals $R^1$ and $R^2$ may be identical or different and each is cyclohexyl or aralkyl of 7 to 12 carbon atoms, each $R^1$ may also be hydrogen, phenyl or alkyl of 1 to 7 carbon atoms, $R^2$ may also be alkyl of 1 to 20, especially of 1 to 7, carbon atoms, which may be substituted by di-(hydroxyethyl)-amino, phenoxy or cyclohexoxy groups, or may be alkoxyalkyl of 3 to 40, especially 3 to 14, carbon atoms, of which preferably 1 to 20, especially 1 to 7, carbon atoms are in the alkoxy group, or may be alkyl or alkenyl of 4 to 20, especially 4 to 8, carbon atoms, which is interrupted by the

group, or may be $R^5-O-(CH_2-CH_2-O)_w(CH_2-CH_2)$, where $R^5$ is hydrogen or alkyl of 1 to 14 carbon atoms and w is an integer, especially from 1 to 14, or may be alkylene containing n radicals

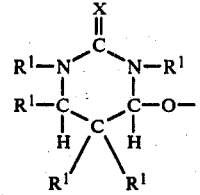

or alkylene containing n-y radicals

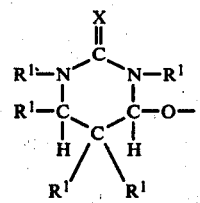

and y hydroxyl groups, alkylene being of n+1 to n+12, especially of n+1 to n+6, carbon atoms, n is 1, 4 or 5, y is 0 or an integer from 1 to 5, X is oxygen or sulfur, $R^3$ is hydrogen and may also, if $R^2$ is an aliphatic radical f at least 5 carbon atoms or a cycloaliphatic or araliphatic radical, be alkyl of 1 to 3 carbon atoms, and $R^4$ has the same meaning as $R^2$ or, if $R^2$ is one of the above preferred alkylene radicals, which contain n or n-y radicals

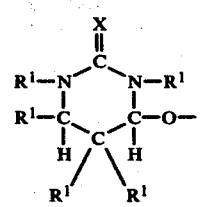

may also be a corresponding alkylene radical which contains n or n+y hydroxyl groups and is of n+1 to n+12, especially of n+1 to n+6, carbon atoms. The above radicals and rings may in addition be substituted by groups which are inert under the reaction conditions, for example alkyl of 1 to 4 carbon atoms.

The following hexahydropyrimidines are examples of suitable starting materials II: 4-hydroxy-2-oxo-hexahydropyrimidine, 5,5-dimethyl-, 5,5-diethyl-, 5,5-di-n-propyl-, 5,5-diisopropyl-, 5,5-di-n-butyl-, 5,5-di-sec.-butyl-, 5,5-diisobutyl-, 5,5-di-tert.-butyl-, 5-phenyl-5-methyl-, 5-benzyl-5-methyl-, 5-cyclohexyl-5-methyl- and 5-methyl-5-isopropyl-4-hydroxy-2-oxo-hexahydropyrimidine; corresponding 4-hydroxy-2-oxo-hexahydropyrimidines which in the 5-position are unsubstituted, monosubstituted or disubstituted by the above groups and in the 1-, 3- and/or 6-position are substituted by methyl, ethyl, hydroxyethyl, n-propyl, isopropyl, n-butyl, isobutyl, sec.-butyl, tert.-butyl, cyclohexyl, benzyl or phenyl; homologous 4-methoxy-, 4-ethoxy-, 4-n-propoxy- and 4-isopropoxy-2-oxo-hexahydropyrimidines; and corresponding 2-thiono-hexahydropyrimidines which are unsubstituted and/or substituted in the positions mentioned above.

Preferred starting materials II are:

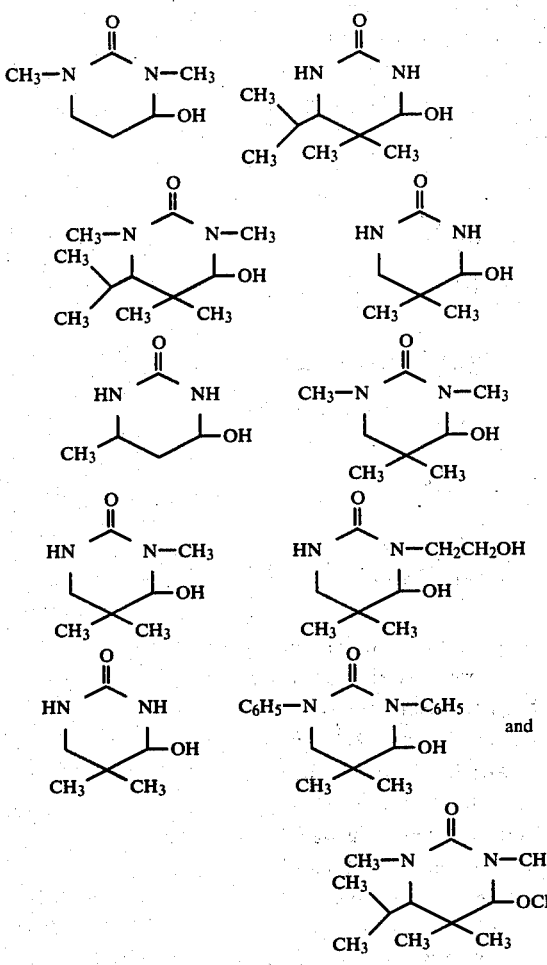

Examples of suitable alcohols III are: undecanol, dodecanol, nonanol, n-hexanol, 2-ethylhexanol, cyclohexanol, benzyl alcohol and ethylene glycol; diglycol, triglycol, tetraglycol, pentaglycol, hexaglycol, heptaglycol, octaglycol, nonaglycol, decaglycol, undecaglycol, dodecaglycol, tridecaglycol, tetradecaglycol, propane-1,3-diol, butane-1,4-diol, propane-1,2-diol, neopentylglycol, 2,4-pentylene glycol, 2,3-butylene glycol, hexane-1,6-diol and corresponding monoethers with alkyl of 1 to 18 carbon atoms; cyclopentanol, cycloheptanol, phenylethyl alcohol, n-pentanol, phenylpropanol, cyclooctanol, n-heptanol, n-octanol, n-decanol and triethanolamine; the methyl, ethyl, propyl, isopropyl, butyl, sec.-butyl, isobutyl and tert.-butyl monoethers of ethylene glycol; glycerol, butanetriols, hexanetriols, pentaerythritol, 2-methyl-2-methylol-propane-1,3-diol, 2-hydroxymethyl-2-ethyl-propane-1,3-diol, pentoses and hexoses.

Examples of preferred starting materials III are:

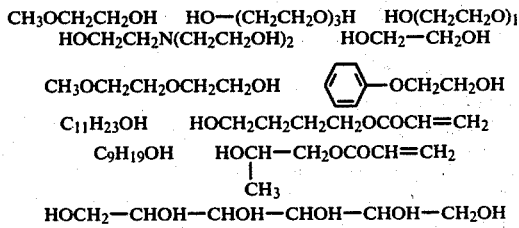

and C₁₃H₂₇O(CH₂CH₂O)₁₂H

The reaction is carried out at above 110° C., expediently at from 110° to 180° C., advantageously at from 120° to 170° C., preferably at from 121° to 160° C., especially at from 125° to 155° C., under atmospheric or superatmospheric pressure, continuously or batchwise. The reaction can be carried out without a solvent; advantageously, however, a solvent which is inert under the reaction conditions, and in particular a solvent which boils above 110° C., is used. Where a liquid of boiling point below 110° C. is involved, the reaction must be carried out in a closed vessel under superatmospheric pressure. Examples of suitable solvents are aromatic hydrocarbons, eg. toluene, ethylbenzene, o-, m- and p-xylene, isopropylbenzene and methylnaphthalene, dimethylformamide and mixtures of the above. Preferred solvents are toluene and the xylenes. It is not necessary that the starting materials and end products should be soluble in the solvents. The insolubility of the end product makes working-up particularly easy. Furthermore, it is not absolutely essential to remove the water of reaction which is formed, though it is advantageous to remove it by azeotropic distillation. The solvent is advantageously used in an amount of from 100 to 10,000 percent by weight, preferably from 400 to 1,000 percent by weight, based on starting material II. The reaction can advantageously be carried out in the absence of a solvent if one or both starting materials or the end product are or is liquid, or fusible at the reaction temperature.

The reaction is advantageously carried out without added acid, if only to allow simpler and more economical operation. It is however possible to add, where appropriate, an acid, for example sulfuric acid, advantageously in a catalytic amount, preferably in an amount of from 0.005 to 0.01 equivalent of acid per mole of starting material II, or a base, for example in the form of sodium hydroxide solution, advantageously in a catalytic amount, preferably in an amount of from 0.005 to 0.01 equivalent of base per mole of starting material II.

The reaction can be carried out as follows: a mixture of the starting materials II and III, advantageously together with solvent, is kept at the reaction temperature for from 0.25 to 3 hours, especially from 0.25 to 1 hour. The end product is then isolated from the mixture in the conventional manner, for example by filtration and crystallization, or by distillation.

The hexahydropyrimid-4-yl ethers obtainable by the process of the invention are valuable starting materials for the preparation of dyes, pesticides and assistants for use in textile chemistry, surface-coating resin chemistry and the timber industry. Their N-methylol and N-alkoxymethyl compounds may be used with advantage as reactive crosslinking agents in textile chemistry, surface-coating resin chemistry and the timber industry.

In the Examples, parts are by weight.

EXAMPLE 1

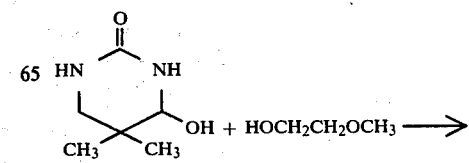

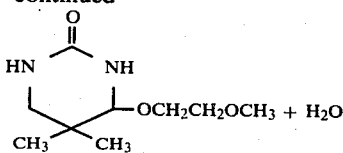

288 parts of 2-oxo-4-hydroxy-5,5-dimethyl-hexahydropyrimidine, 152 parts of methylglycol and 600 parts of xylene are refluxed (at 132° C.) for half an hour in an apparatus equipped with a stirrer, water separator, reflux condenser and heater. The water of reaction which is formed is removed from the reaction mixture by azeotropic distillation, using the water separator. After the xylene has been distilled off, 398 parts of 2-oxo-4-methoxyethoxy-5,5-dimethyl-hexahydropyrimidine are obtained as a crystalline product. This corresponds to a yield of 99% of theory. Melting point (after recrystallization from methylglycol) 112° C.

EXAMPLE 2

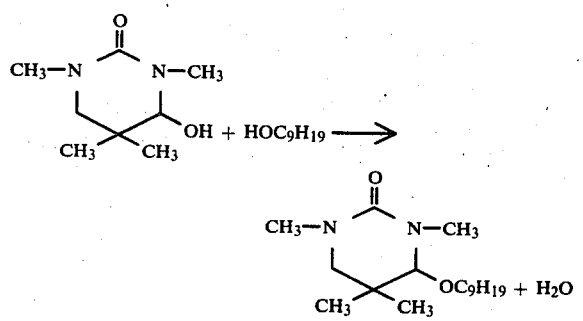

Using the method of Example 1, 172 parts of 2-oxo-4-hydroxy-1,3,5,5-tetramethyl-hexahydropyrimidine and 144 parts of n-nonyl alcohol in 500 parts of xylene are refluxed (at 130°-135° C.) for 40 minutes, whilst removing the water of reaction azeotropically, using the water separator. After evaporating off the xylene, 288 parts of 2-oxo-4-nonoxy-1,3,5,5-tetramethyl-hexahydropyrimidine are obtained. This corresponds to a yield of 96% of theory. Boiling point 154°-158° C./0.2 mbar.

EXAMPLE 3

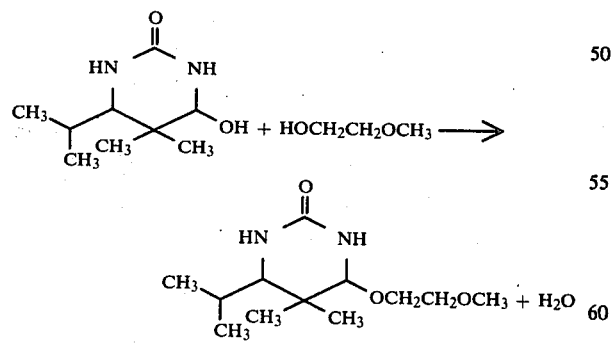

Using the method described in Example 1, 1,116 parts of 2-oxo-4-hydroxy-5,5-dimethyl-6-isopropyl-hexahydropyrimidine and 456 parts of methylglycol in 2,000 parts of xylene are refluxed (at 130°-135° C.) for one hour. The water of reaction formed (108 parts) is removed, using the water separator. After evaporating off the xylene, 1,408 parts of 2-oxo-4-(methoxy-ethoxy)-5,5-dimethyl-6-isopropyl-hexahydropyrimidine are obtained in a crystalline form. This corresponds to a yield of 96% of theory. Melting point (after recrystallization from acetone) 112°-113° C.

EXAMPLE 4

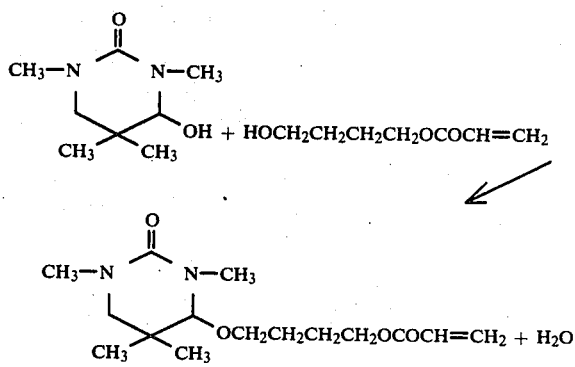

Using the method described in Example 1, a mixture of 344 parts of 2-oxo-4-hydroxy-1,3,5,5-tetramethyl-hexahydropyrimidine and 288 parts of butanediol monoacrylate in 1,000 parts of xylene is refluxed (at 130°-135° C.) for one hour, whilst stirring, the water of reaction being removed, using the water separator. 36 parts of water are eliminated. After evaporating off the xylene, 576 parts of 2-oxo-1,3,5,5-tetramethyl-pyrimid-4-yl ether of butanediol monoacrylate are obtained. This corresponds to a yield of 97% of theory. Boiling point 155°-158° C./0.2-0.3 mbar.

EXAMPLE 5

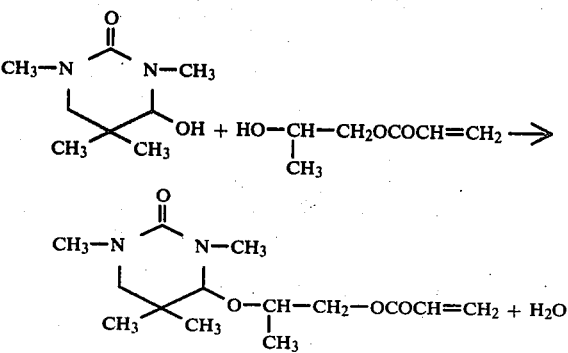

Using the method described in Example 1, 172 parts of 2-oxo-4-hydroxy-1,3,5,5-tetramethyl-hexahydropyrimidine and 130 parts of 2-hydroxy-isopropyl acrylate in 500 parts of xylene are refluxed at 139° C. for one hour. The water of reaction formed (18 parts) is removed, using the water separator. After distilling off the xylene, 281 parts of 2-oxo-1,3,5,5-tetramethyl-pyrimid-4-yl ether of 2-hydroxyisopropyl acrylate are obtained. This corresponds to a yield of 99% of theory. Boiling point 136°-138° C./0.2-0.4 mbar.

EXAMPLE 6

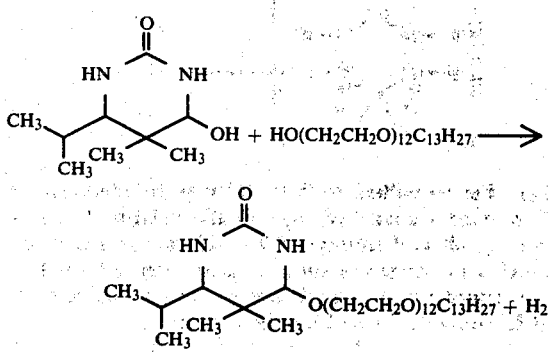

Using the method described in Example 1, a mixture of 18.6 parts of 2-oxo-4-hydroxy-5,5-dimethyl-6-isopropyl-hexahydropyrimidine, 73 parts of an adduct of tridecyl alcohol with 12 moles of ethylene oxide and 300 parts of xylene is refluxed (at 130°–135° C.) for one hour, whilst azeotropically distilling off the water of reaction formed. After evaporating off the xylene, 88 parts of 2-oxo-5,5,6,6-tetramethyl-pyrimid-4-yl ether of the adduct of tridecyl alcohol with 12 moles of ethylene oxide are obtained. The yield is 97% of theory.

EXAMPLE 7

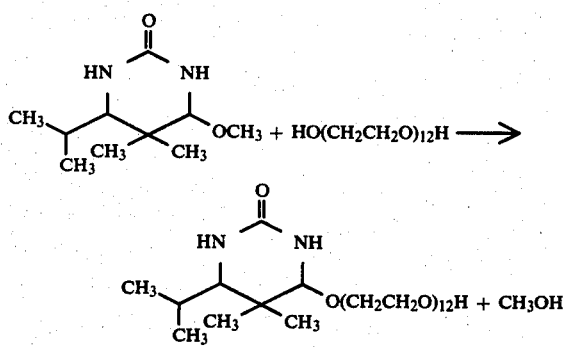

Using the method described in Example 1, 200 parts of 2-oxo-4-methoxy-5,5-dimethyl-6-isopropyl-hexahydropyrimidine and 546 parts of dodecaethylene glycol are heated for one hour at 152° C., whilst stirring and distilling off the methanol eliminated. 702 parts (98% of theory) of 2-oxo-5,5,6,6-tetramethyl-pyrimid-4-yl ether of dodecaethylene glycol are obtained.

EXAMPLE 8

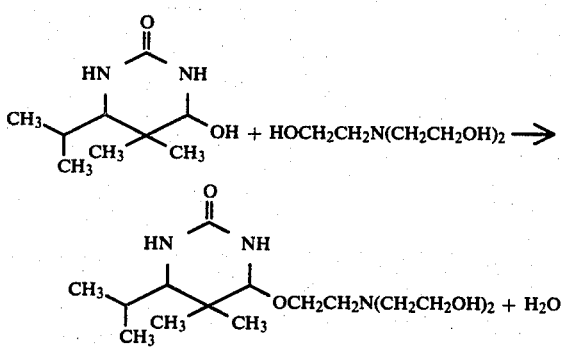

Using the method described in Example 1, 372 parts of 2-oxo-4-hydroxy-5,5-dimethyl-6-isopropyl-hexahydropyrimidine and 298 parts of triethanolamine in 800 parts of xylene are refluxed (at 130°–135° C.) for 2 hours, during which 36 parts of water are removed, using the water separator. After evaporating off the xylene, 621 parts of 2-oxo-5,5,6,6-tetramethyl-pyrimid-4-yl monoether of triethanolamine are obtained. This corresponds to a yield of 98% of theory.

EXAMPLE 9

Using the method described in Example 1, 372 parts of 2-oxo-4-hydroxy-5,5-dimethyl-6-isopropyl-hexahydropyrimidine and 182 parts of sorbitol in 800 parts of xylene are refluxed (at 137° C.) for 3 hours, during which 36 parts of water are removed, using a water separator. After evaporating off the xylene, 511 parts of sorbitol in which two hydroxyl groups have been replaced by two 2-oxo-5,5-dimethyl-6-isopropyl-hexahydropyrimidin-4-oxy radicals are obtained. The end product decomposes above 220° C.

EXAMPLE 10 (USE)

202 parts of the 2-oxo-4-methoxy-ethoxy-5,5-dimethyl-hexahydropyrimidine obtained as described in Example 1 are mixed with 150 parts of a 40 percent strength by weight formaldehyde solution in a stirred apparatus, and after bringing the pH to 10–11 with sodium hydroxide solution, the mixture is heated for 2 hours at 50° C., whilst stirring. It is then neutralized with dilute sulfuric acid and water is added to obtain a 50 percent strength by weight solution. 524 parts of a 50 percent strength by weight aqueous solution of 2-oxo-1,3-bis-hydroxymethyl-4-methoxyethoxy-5,5-dimethyl-hexahydropyrimidine are thus obtained.

A bleached and mercerized poplin cotton fabric weighing 125 g per square meter is then impregnated by padding with a solution of the following composition: 300 parts of a 50 percent strength by weight aqueous solution of 2-oxo-1,3-bis-hydroxymethyl-4-methoxyethoxy-5,5-dimethyl-hexahydropyrimidine, 30 parts of a 40 percent strength by weight aqueous emulsion of a copolymer of 89 parts of n-butyl acrylate, 5 parts of butanediol diacrylate, 3 parts of N-methylol methacrylamide and 3 parts of acrylamide, 1 part of an adduct of 7 parts of ethylene oxide with 1 mole of i-octylphenol, 30 parts of an aqueous-alcoholic solution of an oxyethylated polyamide and 20 parts of magnesium chloride hexahydrate, diluted to 1,000 parts by volume with water. The wet pick-up is from 70 to 75 percent. The fabric is dried on a tenter frame at 100°–110° C. and is then heated on the frame for 5 minutes at 155° C. The finished fabric exhibits the following technological properties:

Dry crease angle according to DIN 53,890: Warp-+weft 278° (untreated fabric: 65)

Wet crease angle according to DIN 53,891: Warp-+weft 270° (untreated fabric: 130)

The smoothness figure of merit, by the Monsanto assessment method, is 3.5–4.

The properties after 5 machine washes at the boil are:

Dry crease angle according to DIN 53,890: Warp-+weft 256° (untreated fabric 76)

Wet crease angle according to DIN 53,891: Warp-+weft 264° (untreated fabric: 134)

Tear strength 40×100 mm weft: 22 kg (untreated fabric: 40).

Tear strength after 5 washes and 5 chlorine treatments:

18 kg (untreated fabric: 39).

I claim:

1. A polyhexahydropyrimid-4-yl ether of the formula

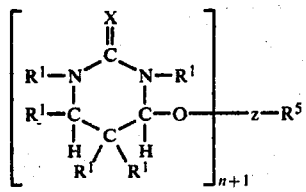

where the individual radicals $R^1$ may be identical or different and each is hydrogen or alkyl of 1 to 7 carbon atom, cyclohexyl, aralkyl of 7 to 12 carbon atoms, or phenyl, X is oxygen or sulfur, n is an integer from 1 to 5, z is a number of single bonds corresponding to n+1 and $R^5$ is alkyl of 1 to 14 carbon atoms.

* * * * *